(12) United States Patent
Herzog et al.

(10) Patent No.: US 10,386,294 B2
(45) Date of Patent: Aug. 20, 2019

(54) METHOD AND DEVICE FOR TUNING OPTICAL MEASUREMENTS ON CONTINUOUSLY MIXED REACTORS

(71) Applicant: Aquila Biolabs GmBH, Baesweiler (DE)

(72) Inventors: Konrad Herzog, Baesweiler (DE); David Frank, Baesweiler (DE)

(73) Assignee: Aquila Biolabs GmBH, Baesweiler (DE)

( * ) Notice: Subject to any disclaimer, the term of this patent is extended or adjusted under 35 U.S.C. 154(b) by 0 days.

(21) Appl. No.: 16/313,719

(22) PCT Filed: Feb. 9, 2018

(86) PCT No.: PCT/EP2018/053239
§ 371 (c)(1),
(2) Date: Dec. 27, 2018

(87) PCT Pub. No.: WO2018/149739
PCT Pub. Date: Aug. 23, 2018

(65) Prior Publication Data
US 2019/0154567 A1    May 23, 2019

(30) Foreign Application Priority Data
Feb. 17, 2017  (DE) .......................... 10 2017 001 588

(51) Int. Cl.
*G01N 21/25*  (2006.01)
*C12M 1/00*  (2006.01)
(Continued)

(52) U.S. Cl.
CPC ............ *G01N 21/253* (2013.01); *B01J 19/28* (2013.01); *C12M 41/06* (2013.01);
(Continued)

(58) Field of Classification Search
CPC ...... G01N 21/253; G01N 21/85; G01N 21/75; G01N 15/0205; G01N 21/51;
(Continued)

(56) References Cited

U.S. PATENT DOCUMENTS

2005/0019900 A1    1/2005  Broyer et al.
2008/0312843 A1   12/2008  Esteban et al.
2013/0033272 A1    2/2013  Folgeroe et al.

FOREIGN PATENT DOCUMENTS

DE    10 2004 017 039 A1    11/2005
DE    10 2011 000 891 A1     8/2012
(Continued)

OTHER PUBLICATIONS

Schmidt-Hager et al. "Noninvasive Online Biomass Detector System for Cultivation in Shake Flasks," Engineering in Life Sciences, Jul. 24, 2014, 14(5):467-476.
(Continued)

*Primary Examiner* — Hina F Ayub
(74) *Attorney, Agent, or Firm* — Wagenknecht IP Law Group, PC

(57) ABSTRACT

A method for tuning optical measurements on continuously mixed reactors, wherein a content of the reactor has at least one optically detectable measured variable, which is carried out by at least one optical measuring arrangement, wherein at least one optical measurement is tuned to a form, distribution, or movement state of at least one phase of the reactor content, wherein mixing the reactor content causes local changes in the permittivity within the reactor, which is detected at at least one location having a known distance from the at least one optical measuring arrangement to be tuned based on a permittivity signal, and wherein the detected permittivity signal of at least one location having a known distance from the at least one optical measuring
(Continued)

arrangement to be tuned is used to tune at least one optical measurement to the form, distribution, or movement state of the reactor content.

11 Claims, 3 Drawing Sheets

(51) Int. Cl.
    *G01N 15/02*     (2006.01)
    *G01N 21/51*     (2006.01)
    *G01N 21/75*     (2006.01)
    *G01N 21/85*     (2006.01)
    *B01J 19/28*     (2006.01)
    *G01N 15/00*     (2006.01)
    *G01N 21/03*     (2006.01)
    *G01N 21/84*     (2006.01)
    *C12M 1/34*     (2006.01)
    *G01N 35/00*     (2006.01)

(52) U.S. Cl.
    CPC ......... *G01N 15/0205* (2013.01); *G01N 21/51* (2013.01); *G01N 21/75* (2013.01); *G01N 21/85* (2013.01); *C12M 41/42* (2013.01); *G01N 2015/0053* (2013.01); *G01N 2021/0325* (2013.01); *G01N 2021/8405* (2013.01); *G01N 2035/00524* (2013.01)

(58) Field of Classification Search
    CPC . G01N 2035/00524; G01N 2021/8405; G01N 2021/0325; G01N 2015/0053; B01J 19/28; C12M 41/06; C12M 41/42
    See application file for complete search history.

(56) References Cited

FOREIGN PATENT DOCUMENTS

DE     10 2014 001 284 B3     1/2015
FR     2 867 278 A1     9/2005

OTHER PUBLICATIONS

Patel et al. "Combined Spectrophotometric-Electrochemical Impedance Imaging System for Biofilm Research," Journal of the Association for Laboratory Automation, Feb. 2005, 10(1):16-23.
PCT/EP2018/053239 International Search Report dated Jun. 15, 2018.

METHOD AND DEVICE FOR TUNING OPTICAL MEASUREMENTS ON CONTINUOUSLY MIXED REACTORS

CROSS REFERENCE TO RELATED APPLICATIONS

This is a US national phase application under 35 USC § 371 of international patent application no. PCT/EP2018/053239, filed Feb. 9, 2018, which claims priority to German patent application no. DE 10 2017 001 588.0, filed Feb. 17, 2017, the content of each is herein incorporated by reference in its entirety.

TECHNICAL FIELD

The invention relates to a method and a device for tuning optical measurements on continuously mixed reactors. The invention is applicable in particular for increasing the robustness and reliability of optical measurements, used for process monitoring of the culturing of cells and also chemical reactions, on continuously mixed reactors, in particular shake flasks, microtiter plates, stirred tank fermenters, and reaction vials.

BACKGROUND OF THE INVENTION

Continuously mixed reactors are used in many areas in chemical, biological, and biotechnological industries and research, in particular for carrying out chemical reactions and syntheses and for culturing living cells. These processes are often monitored using optical methods, such as scattered light measurements, absorption measurements, or fluorescence measurements, which are generally characterized by the combination of at least one light source and at least one light sensor. Robust optical measuring methods require reproducible measuring conditions, in particular with regard to the sample present in the optical path. Any change in this measuring condition and any modification of the optical path between the light source and the light sensor adversely affects the quality and reliability of the optical measurement.

Continuously mixed reactors are characterized by moving components, which make it more difficult to carry out robust and reliable measurements due to the hindrance in setting reproducible measuring conditions through a stable, comparable optical path. In agitated reactors, in particular in shake flasks, shake bottles, fermentation bags, reaction vials, and microtiter plates, the form and distribution of the reactor content changes continuously, thus making optical measurements more difficult. In stirred reactors, although the form and distribution of the reactor content are usually constant, they contain moving stirrers that may likewise interfere with optical measurements and make them more difficult.

PRIOR ART

Methods and devices are known from the prior art which improve the practicability of optical measurements on continuously mixed reactors, in that they attempt in various ways to create reproducible measuring conditions or to incorporate the changes in the optical path into the evaluation of the measuring signals.

DE 102004017039 A1 discloses a method and a device for detecting process parameters in multiple shaken microreactors. As measures for tuning the optical measurement, the first mentioned is the use of a flash lamp as a light source, whose light flashes are coordinated with the rotational movement of the shaker or with a position sensor (acceleration sensor, photoelectric barrier sensor, or Hall sensor) to prevent optical measurements from being carried out in moments when no liquid is present above the sensor and the light source. In addition, one embodiment is disclosed in which a large number of measuring points is recorded, using a high flash frequency and measurement frequency above the shaking frequency of the shaker, to prevent beat amplitudes of the measuring signal.

DE 102014001284 B3 discloses a method, a device, and a system for automated determination of optical densities or the change in optical densities of reaction mixtures in agitated reactors. No tuning of the optical measurement is performed here; instead, continuous optical measurements are carried out at high frequency, wherein the fluctuations of the optical signal are interpreted as fluctuations of the form and distribution of the liquid in the reactor, assuming a constant measured variable, so that an adapted mathematical evaluation and correction of the optical signals may take place using this information.

DE 102011000891 A1 discloses a method and a device for determining a variable of a sample present in a moving container. The cited document describes tuning of the optical measurement to the movement state of the sample to prevent optical measurements from being carried out in moments when too little or no liquid is present above the sensor and the light source. For this purpose, a synchronization means is disclosed which detects the defined movements of the reactor by measuring the acceleration or position, or by detecting the motor movement during the agitation. It is also disclosed that further parameters such as viscosity, shaking frequency, shaking radius, reactor geometry, and filling volume may be used for determining the instantaneous liquid state. Furthermore, one embodiment is disclosed in which detection is carried out directly via an additional optical measurement in order to tune the movement state of the sample.

The methods and devices disclosed by the prior art, which are intended to improve the practicability of optical measurements on continuously mixed reactors, have disadvantageous limitations to their applicability, as described below.

Tuning of optical measurements to the movement state of the reactor, such as with acceleration sensors or position sensors and by the coupling to motor parameters, disadvantageously ignores the fact that, due to the inertia of the reactor content, it always lags behind the movement of the reactor, in particular in agitated systems. Although it is possible to calculate a temporal shift in the relative movement between the reactor and the reactor content by using further parameters such as viscosity, shaking frequency, shaking radius, reactor geometry, and filling volume, as disclosed in DE 102011000891 A1, such calculations are vulnerable to any change in these parameters, resulting in significant erroneous determinations of the movement state of the reactor content, and thus, incorrect tuning of the optical measurement. The viscosity and density of the reactor content and the strength of the friction forces between the reactor content and the reactor wall are of major importance for the form, distribution, and movement state of the reactor content. In particular during the culturing of cells, however, these parameters may change significantly (for example, a change in viscosity due to filamentous growth or by elimination of biopolymers), so that neither raw data from acceleration sensors or position sensors nor data derived therefrom, using known parameters, are suitable for evaluating the form, distribution, and movement state of the reactor content. Thus, it is also not possible to carry out correct tuning of optical measurements.

Although it is possible in principle to detect the form, distribution, and movement state of the reactor content during continuous shaking operation using optical measurements, these optical measuring methods are very vulnerable to external influencing factors that frequently change during the process, which ultimately results in faulty assessment of the form, distribution, and movement state of the reactor content, so that it is no longer possible to carry out correct tuning of the actual optical measurements. Such disadvantageous influencing factors include, among others, interfering external light, variations in the positioning of the reactor above the optical sensor, different reactor materials, and optical inhomogeneities of these materials, changing optical properties of the reactor content, etc. As a result of the large number of external factors influencing optical detection of the form, distribution, and movement state of the reactor content, in many cases it is no longer possible to distinguish whether a change in the optical signal of such devices has been caused by a change in the form, distribution, or movement state of the reactor content, or whether the change in signal is the result of changing or otherwise inconstant internal or external influencing factors.

All methods and devices disclosed in the prior art, due to their dependency on defined basic conditions (shaking frequency, filling volume, viscosity, laminar flow behavior, for example), have further drawbacks that disadvantageously limit their usability for tuning optical measurements on continuously mixed reactors.

The baffles and flow obstructions often used for improved mixing in reactors (baffle flasks, "flower plates," baffle plates, for example), due to the generation of turbulent flow, result in significant deviations, which are extremely difficult to calculate in real time, from the fluid dynamic criteria that are necessary for calculating the temporal shift between the reactor movement and the movement of the reactor content. As a result, the accuracy of the tuning of optical measurements on continuously mixed reactors is disadvantageously decreased. In addition, such flow obstructions often result in intense bubble or foam formation, which makes impossible or at least significantly complicates optical measurements of the form, distribution, and movement state of the reactor content, in particular at low filling volumes.

In addition, a change in the volume of the reactor content, in particular due to sample withdrawal or addition of substances (fed batch fermentation, pH regulation, antifoam additives, addition of protein expression inductors, for example), disadvantageously influences the methods and devices disclosed from the prior art with regard to the accuracy of the temporal tuning of optical measurements on continuously mixed reactors. The reason is that changes in volume always result in changes in the fluid mechanical conditions in the reactor, which cannot be detected by acceleration sensors and position sensors, and which can be resolved only to a limited extent by optical methods, due to their susceptibility to errors with respect to other external parameters.

SUMMARY OF THE INVENTION

The object of the present invention, therefore, is to provide an improved method for tuning optical measurements on continuously mixed reactors, in particular by means of which the tuning of optical measurements on continuously mixed reactors is made possible in a robust manner and independently of process-related changes in the fluidic or optical parameters of the reactor content. In particular, the aim is to provide a method for tuning at least one optical measurement to the form, distribution, or movement state of the reactor content.

According to the invention, at least one optical measurement is to be tuned to the form, distribution, or movement state of the reactor content. The at least one optical measurement takes place using at least one optical measuring arrangement which usually, but not necessarily, includes, in particular is made up of, at least one light source that irradiates light into the reactor content, and at least one light sensor that detects light from the reactor content.

According to the invention, the reactor content includes at least two incompletely miscible phases, wherein at least two phases differ in their phase-specific permittivity. The reactor content may in particular be made up of these two phases.

Typical multiphase systems with locally differing permittivities result, in particular but not exclusively, when the reactor content contains phases of different states of aggregation, for example air and aqueous solutions or suspensions, or aqueous solutions and moving solids (stirrers, for example). Multiphase systems are also formed by incompletely miscible phases of identical states of aggregation (emulsions, for example).

The mixing of the reactor content and the associated change in movement, form, or distribution of the reactor content relative to the reactor results in particular in an accompanying change in the local permittivity at at least one location within the reactor. This local permittivity, its change, and other values derived from it are a measure of the form, distribution, or movement state of the reactor content or at least of one its phases at the time of detection.

The detection of the form, distribution, or movement state of the reactor content with regard to the optical measuring arrangement to be tuned, which is necessary for tuning optical measurements on continuously mixed reactors, is achieved according to the invention by the spatially resolved detection of local permittivities of the reactor content. In contrast to the prior art, this results in direct detection of the form, distribution, or movement state of the reactor content, which is superior to the methods, known from the prior art, of indirectly detecting the form, distribution, or movement state of the reactor content via acceleration measurements of the reactor or position measurements of the reactor. In contrast to methods known from the prior art for optically estimating the form, distribution, or movement state of the reactor content, the method according to the invention is better suited for tuning optical measurements, since in particular it is not subject to the susceptibility to errors in all optical measuring methods on continuously mixed reactors.

The detection according to the invention of at least one local permittivity of the reactor content takes place at a known distance from at least one optical measuring arrangement.

The permittivity signal of at least one location having a known distance from at least one optical measuring arrangement to be tuned, detected according to the invention by at least one permittivity sensor, is utilized by a control unit to tune at least one optical measurement to the form, distribution, or movement state of the reactor content or at least one of its phases, wherein the method according to the invention makes use of the direct correlation of the local permittivity at a specified location or space within the reactor with the form, distribution, or movement state of the reactor content or at least one of its phases.

In one advantageous embodiment of the invention, the detection of at least one local permittivity takes place continuously or at discrete points in time, at a frequency that is higher than the mixing frequency of the reactor or at a frequency such that the mixing frequency of the reactor is not an integral multiple of the detection frequency.

In one advantageous embodiment of the invention, at least one local permittivity or its change is detected by a permittivity sensor situated in an electrical field whose strength, form, and direction change as a function of the local permittivity and thus as a function of the form, distribution, and movement state of the reactor content. Therefore, all types of capacitive sensors are advantageously usable as permittivity sensors according to the invention. Measuring methods that are usable according to the invention include, in particular but not exclusively, absolute and comparative charge transfer methods, amplitude-modulated methods for detecting the reactive current over the capacitive sensor, and frequency-modulated methods that detect shifts in the resonant frequency of an oscillating circuit or some other oscillator coupled to the sensor.

According to the invention, usable permittivity sensors in some embodiments include one, two, or multiple interacting or self-contained electrodes for coupling and decoupling electrical fields for the purpose of permittivity detection.

In one advantageous embodiment of the invention, no relative movement takes place between the reactor and at least one permittivity sensor.

In one advantageous embodiment of the invention, no relative movement takes place between the reactor and at least one optical measuring arrangement.

In one advantageous embodiment of the invention, no relative movement takes place between at least one permittivity sensor and at least one optical measuring arrangement.

In one advantageous embodiment of the invention, at least one permittivity sensor is situated outside the reactor, and allows in particular the noninvasive detection of the local permittivity and thus the form, distribution, or movement state of the reactor content.

In one advantageous embodiment of the invention, at least one permittivity sensor is electrically shielded in such a way that it detects only changes in the permittivity of the reactor content. In particular, such shielding is advantageous for reducing or eliminating interfering external electrical fields, for example electrical fields that are emitted from the electric drive of a shaker or from sparking devices.

In one advantageous embodiment of the invention, the sensor electrical field may be formed by suitable devices in order to adapt and regulate the spatial resolution or sensitivity of the permittivity sensor.

When modulated methods are used for detecting local permittivities, in one advantageous embodiment of the invention at least one of the modulated parameters is changeable over time, in particular to compensate for or otherwise take into account changes in the local permittivity not caused by the mixing of the reactor content.

When methods are used for detecting local permittivities that use pulsed voltages or currents or some other alternating voltages or alternating currents, in one advantageous embodiment of the invention the frequency range of the pulse frequency or alternating frequency is controllable or selectable in particular in such a way that chemical substances, in particular ions and polar molecules that are not a main component or a main medium of the reactor content, do not influence the detection of local permittivities. The frequency dependency of the permittivity is advantageously usable here.

In one advantageous embodiment of the invention, at least two-thirds of the reactor content is composed of a maximum of two main components whose component-based permittivity remains essentially or entirely constant over the entire time of the process proceeding in the reactor. A typical example of such is the culturing of cells in which more than two-thirds of the reactor content is liquid water and air or some other gas phase.

In one embodiment of the invention, the material composition, which changes during the course of a process proceeding in the reactor, of each phase and the associated change in the phase-specific permittivity are detectable by calibration or drift measurements, and the detection of the form, distribution, or movement state of the reactor content is adjustable or correctable using these values.

In one advantageous embodiment of the invention, additional local measuring data of other sensors may be included in the detection of the form, distribution, or movement state of the reactor content, in particular, but not exclusively, data of acceleration sensors, position sensors, and optical sensors.

In one advantageous embodiment of the invention, the claimed method includes methods for predicting the form, distribution, or movement state of the reactor content, in particular, but not exclusively, Kalman filters and comparable Bayesian estimation methods as well as regression and extrapolation methods.

In one advantageous embodiment of the invention, the particular local permittivity at two or more positions having a known distance from at least one optical measuring arrangement to be tuned is detected, so that in particular a more detailed image of the form, distribution, or movement state of the reactor content results, and the tuning of at least one optical measurement may take place more accurately.

In one advantageous embodiment of the invention, the form, distribution, or movement state of at least one phase of the reactor content over at least one optical measuring arrangement is incorporated into the evaluation calculations and analysis of the measuring data of the particular optical measuring arrangement. This allows in particular the correction of the optical measuring data with regard to small positioning differences of the reactor and the particular optical measuring arrangement between two or more otherwise identical measuring arrangements according to the invention.

In one advantageous embodiment of the invention, the formation or the disappearance of new phases or phase systems, for example the formation of foams or water-oil emulsions, may be detected by recording the time-dependent change in at least one local permittivity.

In one advantageous embodiment of the invention, via the detection of the time-dependent change in at least one local permittivity the increase or decrease in the volume portion of at least one phase of the reactor content may be detected, which in particular is observed due to the addition of substances (feeding, pH regulation, induction means, anti-foaming agents) or due to the removal of reactor content components (sampling, partial harvesting) or due to changes in the state of aggregation (for example, evaporation, dissolution, precipitation, crystallization, melting, condensation, etc.) and optionally, associated escape from the reactor.

In one advantageous embodiment of the invention, the detection of the time-dependent change in at least one local permittivity allows the assessment or derivation of further parameters of the reactor content, in particular, but not exclusively, the viscosity and other fluid mechanical parameters.

The present invention is explained in greater detail with reference to the figures and exemplary embodiments.

DETAILED DESCRIPTION OF PREFERRED EMBODIMENTS

A. Definitions

Figure 1:
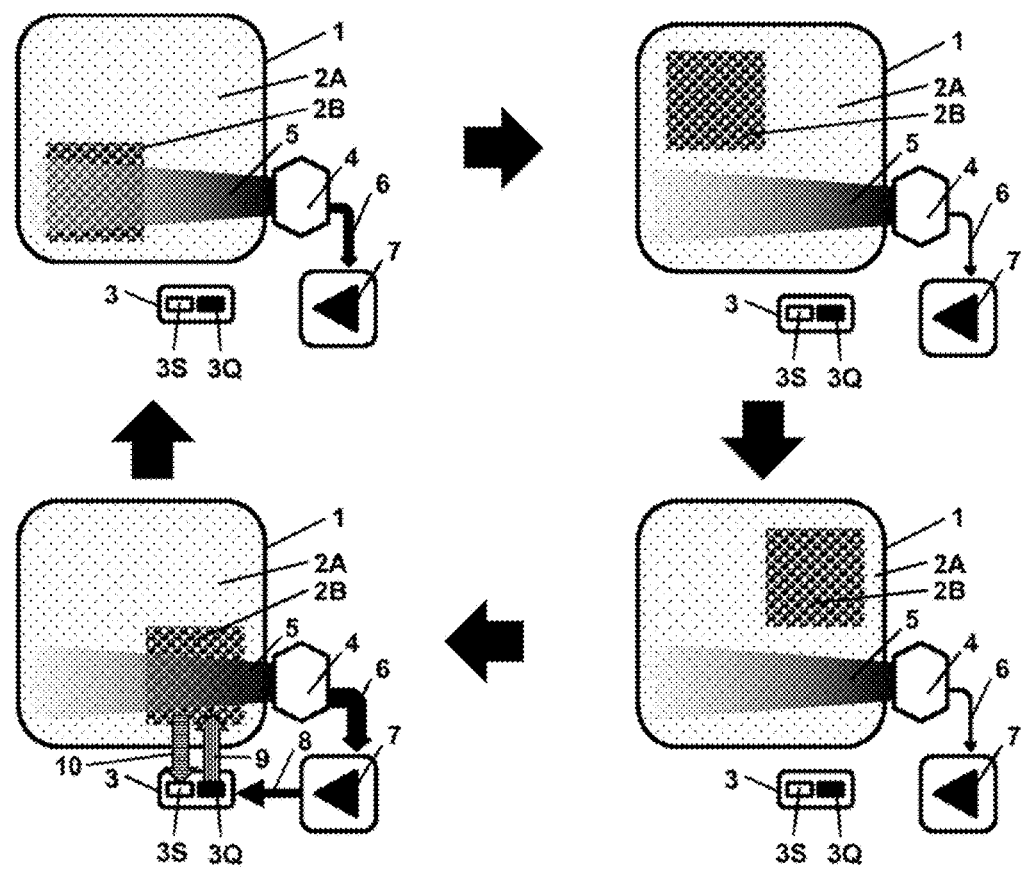
FIG. 1 shows a schematic block diagram of the method according to the invention, using a device according to the invention.

To ensure clarity of several terms used in the description, these terms are defined and explained below and over the course of the description.

A reactor is in particular a container that may be used in particular for culturing organisms or for carrying out chemical and biochemical reaction processes. Further fields of application of reactors include, among others, biocatalytic processes using organisms and/or biomolecules, and other chemical and/or physical processes, wherein the term "process" encompasses all types of conversion, separation, combination, mixing, changing the size of in particular chemical substances, organisms, particles, solutions, emulsions, and foams. Within the meaning of the invention, reactors include in particular stirred tank fermenters, bubble column fermenters, shake flasks, T flasks, microtiter plates, deep well plates, shake vessels, fermentation bags, multipurpose vials, and cell culture dishes. Reactors may be closed or open to their surroundings.

The reactor content encompasses all matter that is present within the outer shell of the reactor. The reactor content encompasses one or more phases and/or is composed of one or more phases.

Mixing a reactor or the reactor content refers in particular to any method for influencing the reactor content in such a way that at least two states, recorded at different times, of the distribution of the reactor content and its components in the reactor are not the same. Common mixing methods make use in particular of mechanical or thermal/thermodynamic processes, in particular but not limited to shaking processes, stirring processes, and diffusion processes. For periodically repeated mixing methods (orbital shaking, rocker shaking, stirring), the mixing frequency is the number of mixing periods per unit time.

The coexistence of incompletely miscible material systems in a reactor content results in the formation of phases. A phase is a material system that is characterized by a dominant state of aggregation and that is not completely miscible with other phases. Typical examples of such are gas phases, liquid phases, and solid phases. Within the meaning of the invention, however, the term "phase" is used not only for pure states of aggregation, but also for material systems characterized by one or more at least substantially homogeneously miscible, suspendable, or emulsifiable material systems or substances. Examples of pure phases are liquid water or gaseous nitrogen. Examples of phases in the expanded scope of definition of the invention according to the above-described criteria are air (gaseous homogeneous mixture), culture medium with cells (virtually homogeneous suspension of cells in a homogeneous aqueous solution of media components such as salts, proteins, carbohydrates, etc.), or a stainless steel mixing turbine (virtually homogeneous mixing of iron and alloying elements). Homogeneity is scale-dependent on the resolution of the permittivity sensors used, so that a homogeneous phase is considered to be present when the permittivity sensor used can no longer detect local changes in permittivity as inhomogeneous. A phase-specific permittivity may be associated with each phase on account of its homogeneity, resulting in a volumetric and molar weighted average value over the relative permittivities of all components of the phase. Named as an example here is the "culture medium with cells" phase, whose average permittivity, as a function of the frequency, results in a weighted average value of the relative permittivities of the main component water in addition to all other components (ions, cells, dissolved molecules, dissolved gases, etc.). Another example of a phase is air, whose average permittivity, as a function of the frequency, results in a weighted average value of the relative permittivities of its components, in particular nitrogen, oxygen, water vapor, carbon dioxide, noble gases, etc.

The combination of phase-specific permittivities with the mixing-related change in the form, distribution, or movement state of at least one phase of the reactor content results in local permittivities and differences in permittivity. Thus, the local permittivity at a location in the reactor where water is present differs significantly from the local permittivity at a location where air is present. Consequently, the detection of local permittivities and local changes in permittivity allows an assessment and/or quantitative recording of the form, distribution, or movement state of the reactor content or at least one phase of the reactor content.

Permittivity sensors detect at least one local permittivity. This takes place in particular via at least one electrical field that interacts with at least one permittivity sensor and also with the reactor content at the location to be examined. The volume of the examined location depends in particular, but not exclusively, on the shape, polarity, and frequency of the electrical field, and on the composition and phase distribution of the reactor content in the interaction region of the electrical field. Permittivity sensors may be implemented in particular as capacitive sensors having one or more electrodes. The electrical field customarily required for the detection of permittivities may be generated either via the sensor electrode itself, or by additional electrodes that interact with the sensor electrode. The positioning of permittivity sensors at a known distance from at least one optical measuring arrangement to be tuned allows detection of the local permittivity with spatial reference to the optical measuring position, so that tuning of the optical measurement to the form, distribution, or movement state of the reactor content or of at least one phase of the reactor content relative to the optical measuring arrangement may take place as a result.

The tuning of an optical measurement to the form, distribution, or movement state of the reactor content encompasses all methods which provide the planning, implementation, processing, evaluation, or display of the optical measurement in conjunction with the form, distribution, or movement state of the reactor content. Within the meaning of the invention, tuning of optical measurements is in particular, but not exclusively, the synchronization of the optical measurement to at least one state of the form, distribution, or movement state of the reactor content, and the incorporation of information concerning the form, distribution, or movement state of the reactor content into the evaluation of the optical measuring data (by correction or normalization, for example). Criteria or limit values concerning detected permittivity signals or values derived therefrom may be used for the purpose of tuning.

Within the meaning of the invention, methods for tuning an optical measurement to the form, distribution, or movement state of the reactor content are carried out or implemented by at least one control unit. In this regard, control units are all devices that associate permittivity signals or values and data derived therefrom concerning the form, distribution, or movement state of the reactor content with the planning, implementation, processing, evaluation, or display of the optical measurement to be tuned. However, within the meaning of the invention, depending on the tuning method, control units in particular are not exclusively operational amplifiers, comparators, PID controllers, Schmitt triggers, and computers. A computer is considered to be any electronic device that can store data (in particular arithmetic and logic data) and process it based on programmable rules. Within the meaning of the invention, computers are considered as, but not limited to, microcontrollers, microprocessors, system on a chip (SoC) computers, PCs, and servers.

B. Description with Reference to the Drawings

FIG. 1 shows a schematic block diagram of the method according to the invention, using a device according to the invention. The device includes a reactor 1 having a reactor content 2. In the schematic illustration in FIG. 1, the reactor content 2 includes two incompletely miscible phases 2A and 2B having different phase-specific permittivities; in particular the reactor content is composed of the two phases. FIG. 1 shows four snapshots from a continuous mixing movement of the reactor 1, which in its course causes a change in the form, distribution, or movement state of the reactor content 2. Situated outside the reactor 1 is at least one optical measuring arrangement 3 whose measurements are to be tuned to the form, distribution, or movement state of the reactor content 2. In one advantageous embodiment of the invention, at least one optical measuring arrangement 3 includes at least one light source 3Q for irradiating light into the reactor content 2, and/or at least one light sensor 3S for detecting light that is emitted from the reactor content 2. The detection of the local permittivity takes place in a specified area of the reactor content 2 via at least one permittivity sensor 4 that interacts with at least one electrical field 5, resulting in at least one permittivity signal 6 that is relayed to a control unit 7. The control unit in turn takes over the tuning 8 of at least one optical measuring arrangement 3. In some embodiments of the invention, the tuning 8 may be an activation signal for at least one optical measuring arrangement 3, as also shown in FIG. 1.

The method according to the invention is apparent in FIG. 1. As the result of mixing, the local permittivity in the reactor 1 changes, so that, by means of the electrical field 5 that interacts with the reactor content 2 and the permittivity sensor 4, and the accompanying detection of the local permittivity in the interaction region of the permittivity sensor 4, information concerning the form, distribution, or movement state of the reactor content 2 is transmitted in the form of a permittivity signal 6 to the control unit 7, which carries out tuning of the optical measurements of at least one optical measuring arrangement 3.

For the embodiment of the invention illustrated in FIG. 1, the tuning 8 takes place in particular as activation of the optical measuring arrangement 3 when the reactor content 2 having dominant phase 2B is situated in front of the optical measuring arrangement 3. The change in the local permittivity which accompanies this movement state and distribution state results in a strong permittivity signal 6, as the result of which the control unit 7 activates the optical measuring arrangement 3 (tuning 8, partial illustration in the lower left corner). In the illustrated embodiment, the tuning 8 takes place by activation of at least one light source 3Q of the optical measuring arrangement 3 to be tuned, so that light 9 is now irradiated from the light source 3Q into the reactor content 2, in particular into phase 2B, where it interacts with components of the reactor content 2 and is subsequently detected as incident light 10 on the light sensor 3S. The optical measurement of the optical measuring arrangement 3 is thus tuned to the form, distribution, or movement state of the reactor content 2, and in the illustrated embodiment, in particular by synchronizing the optical measurement to the presence of phase 2B in front of the optical measuring arrangement 3.

Figure 2:
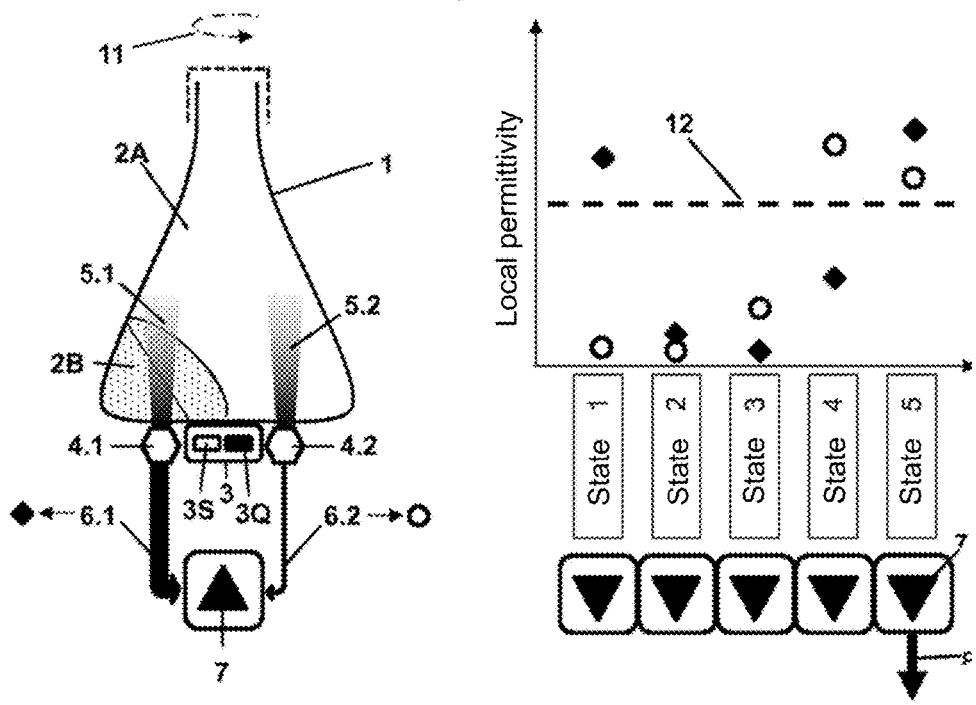
FIG. 2 shows a schematic illustration of a device according to the invention for carrying out the method according to the invention in a shake flask as a reactor for culturing cells.
Figure 2:
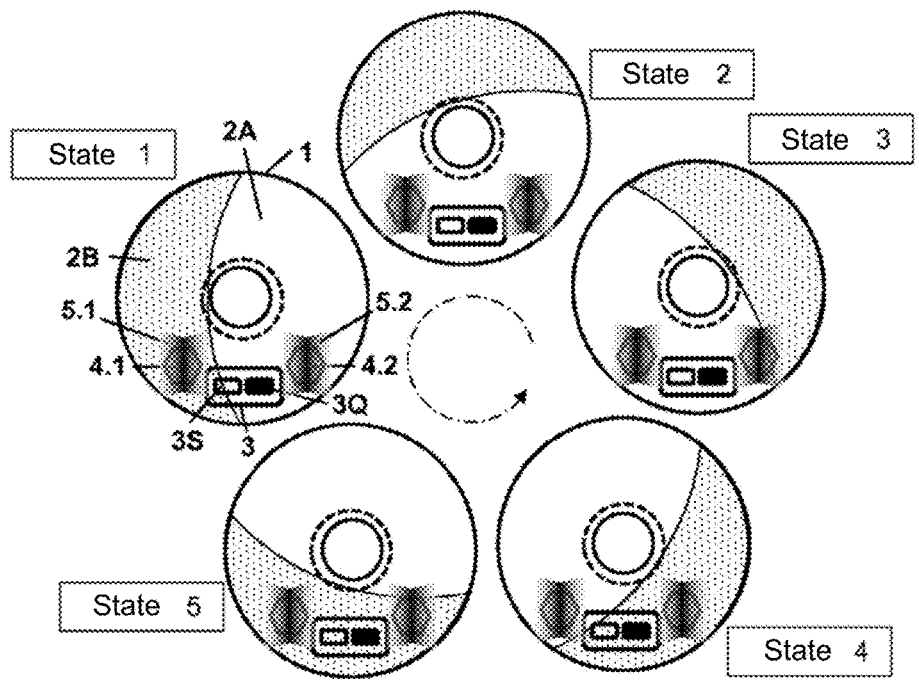

FIG. 2 shows a schematic illustration of a device according to the invention for carrying out the method according to the invention in a shake flask as a reactor 1 for culturing cells. The top left portion of FIG. 2 shows a side view of the measuring arrangement according to the invention. Five exemplary states of the embodiment according to the invention during the course of the shaking movement 11 as an orbital shaking movement are illustrated in the lower portion of FIG. 2. A schematic view of the embodiment from the top is shown. The upper right portion of FIG. 2 shows a schematic diagram that illustrates the particular associated permittivity signal 6.1/6.2 for each of the five movement states discussed below.

A shake flask is used as the reactor 1. The reactor content 2 includes two phases 2A and 2B, 2A being formed by air as a gaseous phase, and 2B, as an overall liquid phase, being composed predominantly of water and various culture media components and cells (culture broth as a suspension of cells in culture medium). For mixing of the reactor content 2, the flask as the reactor 1 carries out a shaking movement 11 that is responsible for a continuous change in the form, distribution, and movement state of the reactor content 2.

Situated beneath the reactor 1 is an optical measuring arrangement 3 whose measurements are to be tuned to the form, distribution, or movement state of the reactor content 2. Within the meaning of the invention and in the field of application of the embodiment of the invention illustrated in FIG. 2, optical measuring arrangements are in particular, but not exclusively, measuring arrangements for detecting the turbidity, cell density, or biomass concentration of phase 2B via scattered light or absorption measurements, as well as measuring arrangements for exciting and/or detecting fluorescence or bioluminescence of certain components of phase 2B or certain fluorescence/luminescence sensors that are at least temporarily in contact with phase 2B (GFP, NADH, proteins, luciferin, and fluorescent pH, oxygen, $CO_2$, glucose, lactate, or metal ion sensors, for example).

The optical measuring arrangement 3 is flanked, tangentially with respect to the shaking movement, by two permittivity sensors 4.1/4.2 which locally interact with the reactor content 2 and its components via a respective associated electrical field 5.1/5.2. In one advantageous embodiment of the invention, as illustrated in FIG. 2, at least two permittivity sensors 4.1/4.2 are situated along the movement path of the mixed reactor content 2. The permittivity sensors 4.1/4.2 detect local changes in permittivity in their vicinity which are caused by the movement of the reactor content 2 and in particular its phases 2A and 2B, and which thus allow an assessment of the local form, distribution, or movement state of the reactor content 2. The resulting permittivity signals 6.1 (solid diamond) and 6.2 (circular ring) are relayed to a control unit 7 which carries out the tuning 8 of the measurements of the optical measuring arrangement 3.

The method according to the invention is implemented in the embodiment in FIG. 2 as follows. Within a shaking period, the permittivity sensors 4.1/4.2 detect the local permittivity of the reactor content 2 multiple times (five times here, as an example). Since the aqueous phase 2B has a much higher relative permittivity than does the air of the gaseous phase 2A, the movement of the liquid for each permittivity sensor 4.1/4.2 results in a characteristic permittivity signal 6.1/6.2 as a function of the particular movement state of the reactor content 2. The greater the local portion of phase 2B in the interaction region of the particular electrical field 5.1/5.2, the greater the permittivity signal 6.1/6.2 of the particular permittivity sensor 4.1/4.2. Based on the known distances between the optical measuring arrangement 3 and the permittivity sensors 4.1/4.2, the control unit 7 can detect the form, distribution, or movement state of the reactor content 2 in spatial reference to the optical measuring arrangement 3, in particular when a certain quantity of aqueous phase 2B is situated above the optical measuring arrangement 3.

The resulting movement-dependent local permittivity signals 6.1/6.2 are schematically illustrated in the upper right portion of FIG. 2. When the tuning 8 of the optical measuring arrangement 3 takes place as activation or deactivation, in one advantageous embodiment of the invention the introduction of at least one boundary condition 12 may be beneficially used, wherein the activation signal as the form of tuning 8 is output by the control unit 7 only when the local permittivity signals 6.1/6.2 meet the boundary condition 12. The boundary condition 12 illustrated in FIG. 2 is formed by a line above which the local permittivity signals 6.1/6.2 must lie in order for activation 8 of the optical measuring arrangement 3 by the control unit 7 to take place. In the illustrated embodiment of the invention, this boundary condition is met only by state 5, so that activation 8 of the optical measuring arrangement 3 takes place only when it is completely covered with phase 2B (culture medium with cells) at a certain minimum height. Tuning 8 of the measurements of the optical measuring arrangement 3 to the form, distribution, and movement state of the reactor content 2 and in particular the aqueous phase 2B is thus achieved by detecting two local permittivities at a known distance from the optical measuring arrangement 3.

Such tuning of optical measurements may be beneficially used, in particular but not exclusively, in continuously agitated reactor systems (shake flasks as well as microtiter plates, shake vessels, T flasks, and shake bags) in order to tune optical measurements directly to the maximum liquid level via at least one optical measuring arrangement, and thus eliminate or reduce external interfering factors such as foam, inhomogeneous phase distributions, or undesirable reflections and scatterings on the reactor wall. The direct detection of the form, distribution, or movement state of the reactor content via the detection of local permittivities or their change is superior to the methods known from the prior art with regard to accuracy, temporal and spatial resolution, calculation effort, and susceptibility to process-related changes in the fluid characteristic of the reactor content 2.

Figure 3:
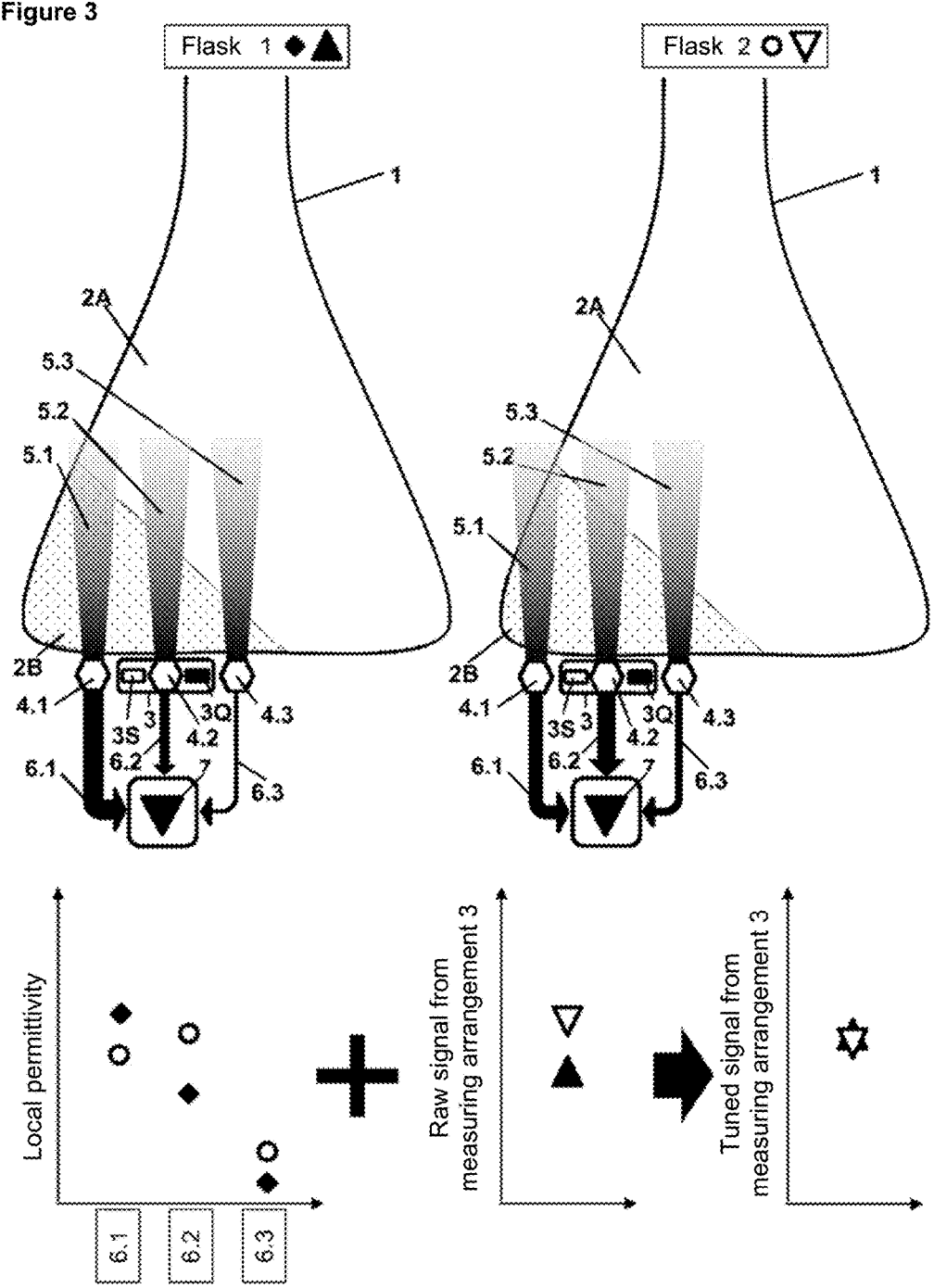
FIG. 3 shows a schematic illustration of a device according to the invention for carrying out the method according to the invention with multiple permittivity sensors.

FIG. 3 shows a schematic illustration of a device according to the invention for carrying out the method according to the invention with multiple permittivity sensors. Two identical devices according to the invention, having two shake flasks as the reactor 1, are illustrated, with different positioning above the optical measuring arrangement 3 and the permittivity sensors 4.1/4.2/4.3.

With regard to the composition of the reactor content 2, the mixing movement, the basic interaction of the permittivity sensors 4.1/4.2/4.3 with the reactor content 2, and the characteristics of the optical measuring arrangement 3, the embodiment of the invention illustrated in FIG. 3 corresponds to the descriptions for FIG. 2. However, in a departure therefrom, three permittivity sensors 4.1/4.2/4.3 are situated at known distances from the optical measuring arrangement 3, the permittivity sensors 4.1/4.3 flanking the optical measuring arrangement radially with respect to the shaking movement, and the permittivity sensor 4.2 being situated between the light source 3Q and the light sensor 3S. Due to the radial arrangement, the permittivity sensors 4.1/4.2/4.3 detect a radial volume range of the reactor content 2, so that the respective permittivity signals 6.1/6.2/6.3 represent a height profile or volume profile of a radial section through the reactor content 2. This is illustrated in the lower left diagram in FIG. 3 for the movement and distribution states of the reactor content 2 shown at the top in FIG. 3; the permittivity signals 6.1/6.2/6.3 for flask 1 are illustrated as solid diamonds, and for flask 2 are illustrated as a circular ring.

The movement state illustrated in FIG. 3 corresponds to state 5 from FIG. 2, in which an activation 8 of the optical measuring arrangement 3 takes place. It is apparent from FIG. 3 that, due to the differences in relative positioning between the optical measuring arrangement 3 and the reactor 1 and reactor content 2, the volume of phase 2B, which is relevant for the optical measurement, changes in the visual field of the optical measuring arrangement, which, despite identical conditions in phase 2 (identical cell density, for example), results in differences in the signal of the optical measuring arrangement 3 (see the bottom center diagram in FIG. 3: solid triangle for flask 1, blank triangle for flask 2).

The tuning 8 according to the invention of optical measurements on continuously mixed reactors 1 therefore also includes the correction of optical signals by means of the permittivity signals 6.1/6.2/6.3 obtained by the local permittivity measurements, and the information derived therefrom concerning the form, distribution, or movement state of the reactor content 2. As illustrated in the lower left diagram in FIG. 3, different local permittivity profiles result, depending on the positioning or filling volume of the reactor 1. According to the invention, these may be utilized, in particular but not exclusively, to derive volume profiles, and to use these to calculate the volume, situated in the visual field of the optical measuring arrangement, of the components of the reactor content 2 (shown as phase 2B in FIG. 3) that are relevant for the optical measurement. On the basis of such calculations, corrective tuning and in particular normalization of the optical measurement to the measurement-relevant volume in the visual field of the optical measuring arrangement 3 are then carried out by the control unit 7. The result is a tuned measuring signal of the particular optical measuring arrangement 3 which is independent of the form, distribution, or movement state, as illustrated in the lower right portion of FIG. 3 (solid triangle for flask 1, blank triangle for flask 2, both overlapping due to tuning with the same Y axis value).

Such normalizing tunings of optical measurements on continuously mixed reactors 1 find application according to the invention in particular for tuning to positioning differences between at least two reactors 1 to be compared, for tuning to different filling volumes or phase portions of the reactor contents 2 of at least two reactors 1 to be compared, and for tuning to different mixing conditions, and thus, differences in the form, distribution, or movement state of the reactor contents 2 of at least two reactors 1 to be compared.

LIST OF REFERENCE NUMERALS

Reference is made to the description and claims for interpretation of the reference numerals.

| | |
|---|---|
| 1 | reactor |
| 2, 2A, 2B | reactor content and phases 2A, 2B with different phase-specific permittivities |
| 3, 3Q, 3S | optical measuring arrangement with light source 3Q and light sensor 3S |
| 4, 4.1, 4.2, 4.3 | Permittivity sensor, multiple permittivity sensors 4.1, 4.2, 4.3 |
| 5, 5.1, 5.2, 5.3 | electrical field in interaction with permittivity sensor 4 and reactor content 2, multiple electrical fields 5.1, 5.2, 5.3 in interaction in each case with reactor content 2 and with permittivity sensor 4.1, 4.2, 4.3 |
| 6, 6.1, 6.2, 6.3 | permittivity signal, signals 6.1, 6.2, 6.3 of the respective permittivity sensors 4.1, 4.2, 4.3 |
| 7 | control unit |
| 8 | tuning of at least one optical measuring arrangement 3 |
| 9 | emitted light from light source 3Q |
| 10 | incident light on light sensor 3S |
| 11 | movement for mixing the reactor content 2 |
| 12 | boundary condition for activating (as tuning 8) the optical measuring arrangement 3 |

The invention claimed is:

1. A method for tuning optical measurements on continuously mixed reactors,
   wherein a reactor content of the reactor has at least one optically detectable measured variable,
   wherein at least one optical measuring arrangement carries out optical measurements of at least one of the optically detectable measured variables,
   wherein the at least one optical measurement is to be tuned to a form, distribution, or movement state of at least one phase of the reactor content,
   wherein mixing the reactor content causes local changes in the permittivity within the reactor,
   characterized in that,
   a local permittivity is detected at at least one location having a known distance from the at least one optical measuring arrangement to be tuned based on a permittivity signal, and
   a detected permittivity signal of at least one location having a known distance from the at least one optical measuring arrangement to be tuned is used to tune the at least one optical measurement to the form, distribution, or movement state of the reactor content.

2. The method according to claim 1, characterized in that the change in at least one local permittivity or some other value derived therefrom is utilized to tune the at least one optical measurement to the form, distribution, or movement state of the at least one phase of the reactor content.

3. The method according to claim 1, characterized in that the tuning of the at least one optical measuring arrangement takes place as activation and deactivation of the optical measuring arrangement as a function of the form, distribution, or movement state of at least one phase of the reactor content in a visual field of the optical measuring arrangement.

4. The method according to claim 1, characterized in that the tuning of the at least one optical measuring arrangement takes place as correction or normalization of the optical measuring signal of the optical measuring arrangement as a function of the form, distribution, or movement state of at least one phase of the reactor content in a visual field of the optical measuring arrangement.

5. The method according to claim 1, characterized in that the detection of the form, distribution, or movement state of the reactor content takes place via multiple permittivity sensors.

6. The method according to claim 1, characterized in that the detection of the at least one local permittivity takes place via at least one electrical field that locally interacts with the reactor content and at least one permittivity sensor.

7. The method according to claim 1, characterized in that the detection of the at least one local permittivity takes place via a capacitive measuring method based on a capacitive permittivity sensor.

8. A device for carrying out the method according to claim 1, characterized in that the device includes at least one permittivity sensor at at least one location having a known distance from the at least one optical measuring arrangement to be tuned, the permittivity sensor being configured for detecting changes in the local permittivity, and the device includes at least one control unit that is configured for carrying out the tuning of the optical measurement to the form, distribution, or movement state of the reactor content or at least one of its phases, based on the at least one permittivity signal of the at least one permittivity sensor.

9. The device according to claim 8, characterized in that the device includes at least one capacitive permittivity sensor that is configured for detecting the at least one local permittivity.

10. The device comprising a control unit configured for controlling a method according to claim 1.

11. The device according to claim 10, characterized in that the device includes at least one capacitive permittivity sensor that is configured for detecting the at least one local permittivity.

* * * * *